US011135376B2

(12) United States Patent
Ploch

(10) Patent No.: US 11,135,376 B2
(45) Date of Patent: Oct. 5, 2021

(54) DOSING MECHANISM FOR MULTI-SHOT INJECTION DEVICE COMPRISING FLEXIBLE RATCHET ELEMENT

(71) Applicant: SANOFI, Paris (FR)

(72) Inventor: Markus Ploch, Frankfurt am Main (DE)

(73) Assignee: Sanofi, Paris (FR)

(*) Notice: Subject to any disclaimer, the term of this patent is extended or adjusted under 35 U.S.C. 154(b) by 500 days.

(21) Appl. No.: 16/084,870

(22) PCT Filed: Mar. 15, 2017

(86) PCT No.: PCT/EP2017/056139
§ 371 (c)(1),
(2) Date: Sep. 13, 2018

(87) PCT Pub. No.: WO2017/158033
PCT Pub. Date: Sep. 21, 2017

(65) Prior Publication Data
US 2019/0091413 A1    Mar. 28, 2019

(30) Foreign Application Priority Data
Mar. 15, 2016  (EP) .................................... 16305275

(51) Int. Cl.
*A61M 5/20*   (2006.01)
*A61M 5/315*  (2006.01)

(52) U.S. Cl.
CPC .......... *A61M 5/31593* (2013.01); *A61M 5/20* (2013.01); *A61M 5/2033* (2013.01);
(Continued)

(58) Field of Classification Search
CPC .......... A61M 5/31583; A61M 5/31585; A61M 5/3155; A61M 5/31553; A61M 5/31593;
(Continued)

(56) References Cited

U.S. PATENT DOCUMENTS

2006/0229570 A1*  10/2006  Lovell .............. A61M 5/31551
                                                              604/218
2007/0244436 A1*  10/2007  Saiki ................ A61M 5/31528
                                                              604/131
(Continued)

FOREIGN PATENT DOCUMENTS

WO   WO 2007/017052    2/2007
WO   WO 2012/067582    5/2012
(Continued)

OTHER PUBLICATIONS

International Preliminary Report on Patentability in Application No. PCT/EP2017/056139, dated Sep. 18, 2018, 6 pages.
(Continued)

*Primary Examiner* — William R Carpenter
*Assistant Examiner* — William R Frehe
(74) *Attorney, Agent, or Firm* — Fish & Richardson P.C.

(57) ABSTRACT

The disclosure provides a dose controlled multi-shot injection device comprising a housing and a dose setting mechanism, wherein the dose setting mechanism includes a drive spring, a rotatable dose setting handle adapted to set a dose of medicament, thereby biasing the drive spring, and a ratchet mechanism for maintaining the drive spring in a biased state against a spring force at a set dose. The ratchet mechanism includes a fixed ratchet element coupled to the housing and having a circumferential teething, a movable flexible ratchet element provided with at least two teethed portions configured to engage the circumferential teething at least pairwise at any one of a plurality of engaging positions, which respectively represent a set dose, and a rotational element coupled to the dose setting handle configured to translate torque from the dose setting handle into a number of forces radially acting on the flexible ratchet element resulting in an elastic deformation of the flexible ratchet (Continued)

element, thereby releasing the engagement between the teethed portion and the circumferential teething.

16 Claims, 6 Drawing Sheets

(52) U.S. Cl.
CPC ...... *A61M 5/3155* (2013.01); *A61M 5/31535* (2013.01); *A61M 5/31583* (2013.01); *A61M 5/31585* (2013.01)

(58) Field of Classification Search
CPC .......... A61M 5/31533; A61M 5/31545; A61M 5/31548
See application file for complete search history.

(56) References Cited

U.S. PATENT DOCUMENTS

| | | | | |
|---|---|---|---|---|
| 2008/0147005 A1* | 6/2008 | Moller | ................ | A61M 5/3155 604/134 |
| 2012/0283647 A1* | 11/2012 | Cronenberg | ...... | A61M 5/31595 604/207 |
| 2014/0249482 A1* | 9/2014 | Wieselblad | ....... | A61M 5/31535 604/211 |
| 2016/0089500 A1* | 3/2016 | Soerensen | ......... | A61M 5/31528 604/208 |
| 2016/0151574 A1* | 6/2016 | Oakley | ............. | A61M 5/31541 604/208 |
| 2016/0287799 A1* | 10/2016 | Blancke | ............ | A61M 5/31551 |
| 2017/0312443 A1* | 11/2017 | Avery | ................ | A61M 5/31585 |
| 2019/0366009 A1* | 12/2019 | Hewson | ............ | A61M 5/31553 |
| 2020/0306451 A1* | 10/2020 | Knowles | ................ | A61M 5/315 |

FOREIGN PATENT DOCUMENTS

| | | |
|---|---|---|
| WO | WO 2014/187812 | 11/2014 |
| WO | WO 2015/007821 | 1/2015 |

OTHER PUBLICATIONS

International Search Report and Written Opinion in Application No. PCT/EP2017/056139, dated Jun. 9, 2017, 8 pages.

* cited by examiner

… …

DOSING MECHANISM FOR MULTI-SHOT INJECTION DEVICE COMPRISING FLEXIBLE RATCHET ELEMENT

CROSS REFERENCE TO RELATED APPLICATIONS

This application is a U.S. national stage application under 35 USC § 371 of International Application No. PCT/EP2017/056139, filed on Mar. 15, 2017, which claims priority to European Application No. 16305275.6, filed on Mar. 15, 2016, the entire contents of which are incorporated herein by reference.

TECHNICAL FIELD

The disclosure generally relates to an injection device and more particular to a dose controlled multi-shot injection device.

BACKGROUND

Self-administered injectable medicaments are often delivered using a variable-dose injection device. Prior to the injection the user selects the dose that may be required according to a prescribed dose and/or to a current or expected future physical condition. Typically such devices allow the user to select any dose from one unit up to a maximum unit dose that the device can deliver.

Pen type injection devices, such as wind-up pens, have been designed and developed to perform regular injections by persons without formal medical training. Because the patient may be using such an injection device, one requirement is that the device should be robust in construction. The injection device may also be easy to use both in terms of the injection device manipulation and understanding of the devices operation. This is of prime importance to patients who are required to inject themselves repeatedly with a medicament component and the volume of the medicament component to be injected may vary from patient to patient and even from injection to injection.

To set a predetermined dose of a medicament component, known injection devices comprise a dose setting mechanism using a drive spring that is biased due to a rotation of a dose setting button or knob. The drive spring will be maintained in a biased state until release.

SUMMARY

The present disclosure provides a dose controlled multi-shot injection device comprising a housing and a dose setting mechanism, wherein the dose setting mechanism includes
   a drive spring,
   a rotatable dose setting member adapted to set a dose of medicament, thereby biasing the drive spring and
   a ratchet mechanism for maintaining the drive spring in a biased state against a spring force at a set dose,
      wherein the ratchet mechanism includes
a fixed ratchet element coupled to the housing and having a circumferential teething,
a movable flexible ratchet element provided with at least two teethed portions configured to engage the circumferential teething at least pairwise at any one of a plurality of engaging positions, which respectively represent a set dose, and a rotational element coupled to the dose setting handle configured to translate torque from the dose setting handle into a number of forces radially acting on the flexible ratchet element resulting in an elastic deformation of the flexible ratchet element, thereby releasing the engagement between the teeth and the circumferential teething.

The dose controlled multi-shot injection device provides an active release of the ratchet mechanism in order to dial down a set dose of medicament in a controlled manner, wherein stored energy from the drive spring may be progressively released. Here, the flexible ratchet element is in engagement with the circumferential teething such that the teethed portions lock against the force of the drive spring in subsequent teeth of the circumferential teething when a torque is applied to the dose setting handle, which results in a rotation of the dose setting handle and the rotational element. Overcoming such a ratchet lock is particularly easy according to the prior art, which leads to a user-friendless handling of the injection device, mainly for elder patients having less power to reduce a set dose prior to injection.

The number of forces acting on the flexible ratchet element may be applied to a perimeter of the flexible ratchet element arranged between the pair of teethed portions. If the flexible ratchet element may be configured at least substantially as an annular structure, the acting forces may be applied in an angular offset to the teethed portions. This allows deflecting the perimeter of the flexible ratchet element radially outwards and thus a release of the engagement between the teethed portions and the circumferential teething is possible.

Furthermore, the number of forces acting on the flexible ratchet element may have the same orientation as an engagement force provided by a structural stiffness of the flexible ratchet element in order to maintain the engagement between the teethed portions and the circumferential teething against the force of the drive spring. The forces acting on the flexible ratchet element may have a component pointing along a radial outward direction and thus having the same orientation as the engagement force that points into a rotation direction of the flexible ratchet element. In an alternative embodiment, the forces acting on the flexible ratchet element have an orientation opposite to the engagement forces provided thereof.

The rotational element may be further comprise a number of cam sections, which rotate together with the dose setting handle but with respect to the flexible ratchet element. The cams translate a torque into the number of forces acting on the flexible ratchet element. This allows a radially deformation of the flexible ratchet element in order to release the ratchet lock.

In an exemplary embodiment, the fixed ratchet element comprises a ring-shape and the circumferential teething is arranged on an inner circumference of the fixed ratchet element. The fixed ratchet element may thus be configured as a gear wheel comprising inner gear flanks. According to this, the flexible ratchet element may comprise an elongated shape with a central elongated slot and two teethed portions arranged opposite each other. The rotational element comprises a shaft and two cams arranged opposite each other within the slot.

In an alternative embodiment, the flexible ratchet element may comprise a triangular shape with a central slot and three teethed portions each arranged on one edge of the flexible ratchet element, wherein three cams are provided on the rotational element within the slot, which may distributed about a circular shaft. Here, the engagement between the teethed portions and the circumferential teething is increased with respect to the engagement provided in the embodiment mentioned before due to the increased number of teethed portions that centers the engagement between the teethed portions and the circumferential teething within the fixed ratchet element. This also enables the use of stronger drive springs.

According to the exemplary embodiments comprising the elongated and triangular-shaped flexible ratchet element, the cams may rotate about an axis defined by the shaft with respect to the flexible ratchet element upon application of torque onto the dose setting handle, thereby deflecting the perimeter of the flexible ratchet element in a radial outward direction in a manner reducing a distance between the teethed portions.

In another exemplary embodiment, the fixed ratchet element is substantially ring-shaped and the circumferential teething is arranged on an outer circumference of the fixed ratchet element. The fixed ratchet element may thus be configured as a gear wheel comprising outer gear flanks.

According to this, the flexible ratchet element may comprise a ring-shape and two teethed portions arranged opposite each other on an inner circumference. The rotational element comprises a ring-shaped shaft and at least four cams, which are distributed about an inner circumference of the shaft and decreasing an inner diameter of the shaft, thereby facing the flexible ratchet element. The flexible ratchet element may be arranged between the rotational element and the fixed ratchet element such that the cams abut the perimeter of the flexible ratchet element and the teethed portions face the circumferential teething. In particular, the flexible ratchet element, the fixed ratchet element and the rotational element are arranged concentrically into each other such that the fixed ratchet element is concentrically arranged within the flexible ratchet element and the flexible ratchet element is concentrically arranged within the rotational element.

Due to the decreased inner diameter of the shaft, the flexible ratchet element may comprise at least two bulges respectively located between the teethed portions.

According to the exemplary embodiment comprising the substantially ring-shaped flexible ratchet element, the cams rotate about an axis defined by the shaft with respect to the flexible ratchet element upon application of torque onto the dose setting handle, thereby pushing the bulges in the same rotation direction as the rotational element is rotated, wherein the teethed portions are disengaged from the circumferential teething when the bulges reaches the teethed portions.

In an exemplary embodiment, the injection device further comprises a rotationally drivable expelling mechanism adapted to linearly urging against a movable component of a medicament container. For example, the movable component is coupled to the medicament container, e. g. a cartridge containing a liquid drug, in a manner that a set dose of medicament is expelled during a linear movement of the movable component, thereby pressing out the medicament component through a needle provided on a distal end of the medicament container.

In an exemplary embodiment, the expelling mechanism includes a spindle-drive converter. For example, the spindle drive converter comprises a rotatable spindle nut rotatable coupled to a threaded plunger.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein.

Corresponding parts are marked with the same reference symbols in all figures.

DETAILED DESCRIPTION OF THE FIGURES

Figure 1:
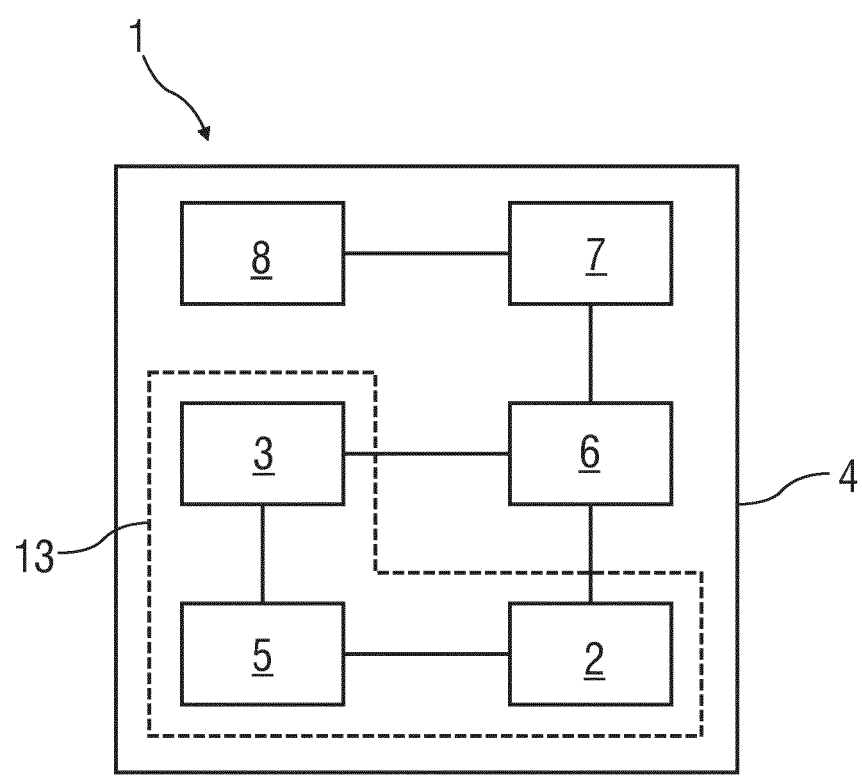
FIG. 1 is a simplified block diagram of a dose controlled multi-shot injection device comprising a ratchet mechanism.

FIG. 1 shows a simplified block diagram of a dose controlled multi-shot injection device 1, wherein only components of importance for the present disclosure are illustrated.

The injection device 1 may be configured as a wind-up pen comprising a drive spring 2, e. g. a torsion spring, which can be strained by rotating a dose setting handle 3 of the injection device 1. The dose setting handle 3 may be configured as a sleeve-like component with a serrated outer skirt and axially constrained to a housing 4 of the injection device 1.

The dose setting handle 3 is a component of a dose setting mechanism 13 that provides a dial up and dial down mechanism. Within the dial up mechanism, the drive spring 2 is strained when setting a dose by rotating the dose setting handle 3 with respect to the housing 4 in a predetermined direction, e. g. clockwise. Within the dial down mechanism, the drive spring 2 will be unstrained when rotating the same dose setting handle 3 in an otherwise direction, e. g. counter clockwise.

In order to maintain stored energy in the strained drive spring 2 after a dose has been set, the injection device 1 comprises a ratchet mechanism 5. The ratchet mechanism 5 provides a ratchet lock acting against a spring force of the strained drive spring 2 at any possible set dose. To dial down a set dose, the spring force has to be overcome, which will be described in in more detail in context with the FIGS. 3 to 6.

Furthermore, the injection device 1 comprises a rotationally drivable expelling mechanism 6 adapted to linearly urging against a movable component 7 coupled to a medicament container 8. For example, the movable component 7 is movable within the medicament container 8, e. g. a cartridge containing a liquid drug, in a manner that the set dose of medicament is expelled during a rotation and/or linear movement of the movable component 7. The medicament will be then pressed out through an injection needle 9 (illustrated in FIG. 2) provided distally on the medicament container 8.

Figure 2:
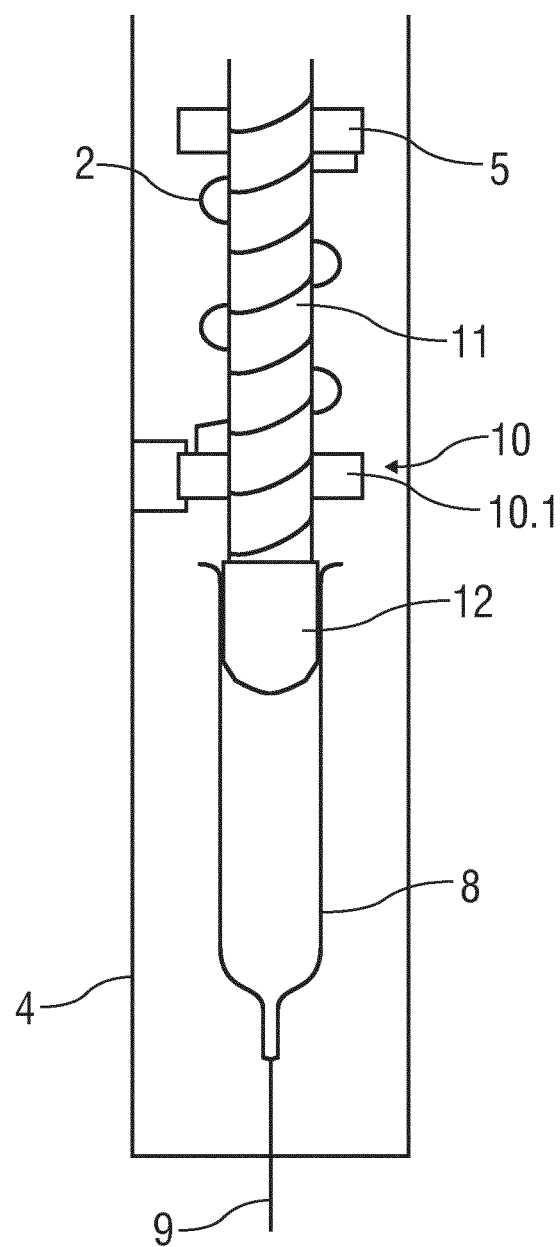
FIG. 2 is a schematic longitudinal section of an exemplary embodiment of a dose controlled multi-shot injection device comprising a spindle-drive converter.

FIG. 2 shows another exemplary embodiment of a dose controlled multi-shot injection device 1, whereby the expelling mechanism 6 comprises a spindle-drive converter 10.

The spindle-drive converter 10 comprises a spindle nut 10.1 that is coupled to the housing 4 and operationally engaged to a threaded plunger 11, wherein the spindle nut 10.1 is allowed to rotate with respect to the threaded plunger 11. The spindle nut 10.1 further fixes a distal end of the drive spring 2. The threaded plunger 11 is axially movable with respect to the spindle nut 10.1 and provides an axially directed force upon a stopper 12 in the medicament container 8 to urge medication from the medicament container 8 through the attached injection needle 9.

Figure 3:
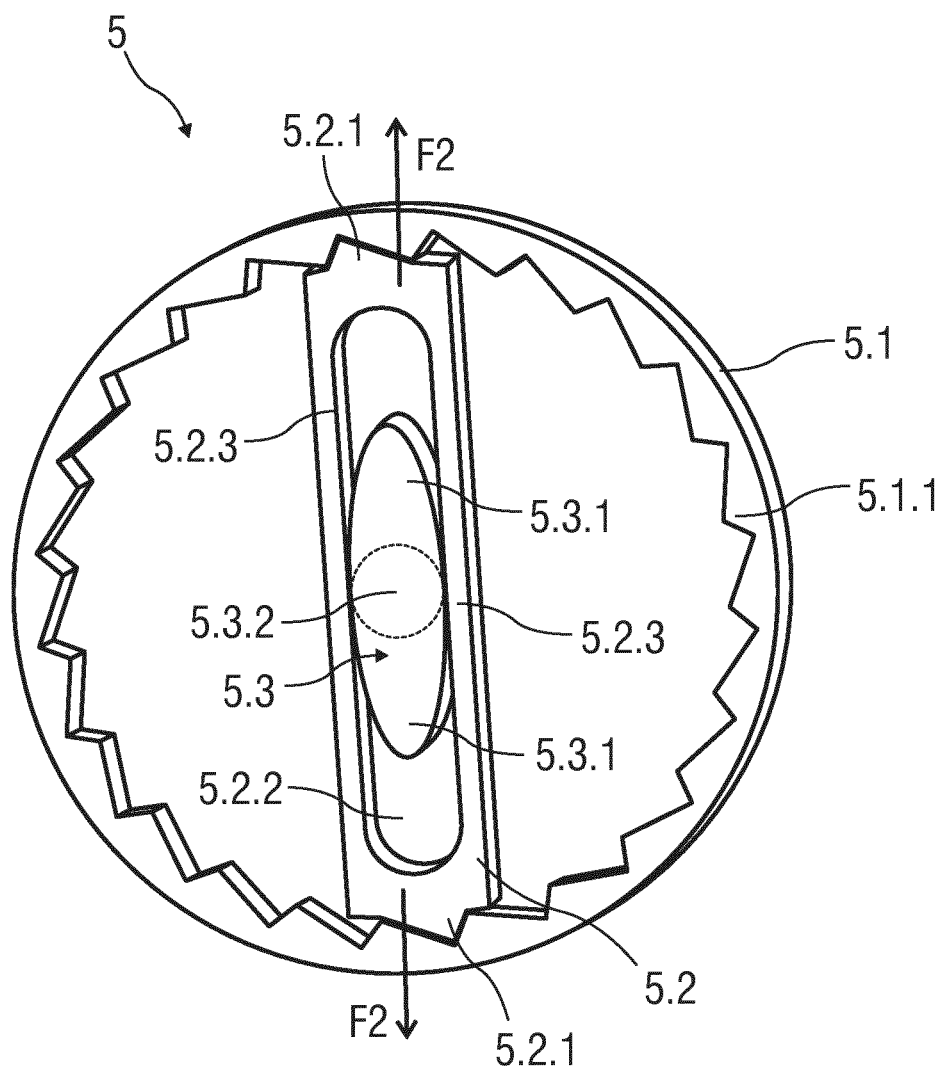
FIG. 3 is a schematic cross section of an exemplary embodiment of a locked ratchet mechanism.
Figure 4:
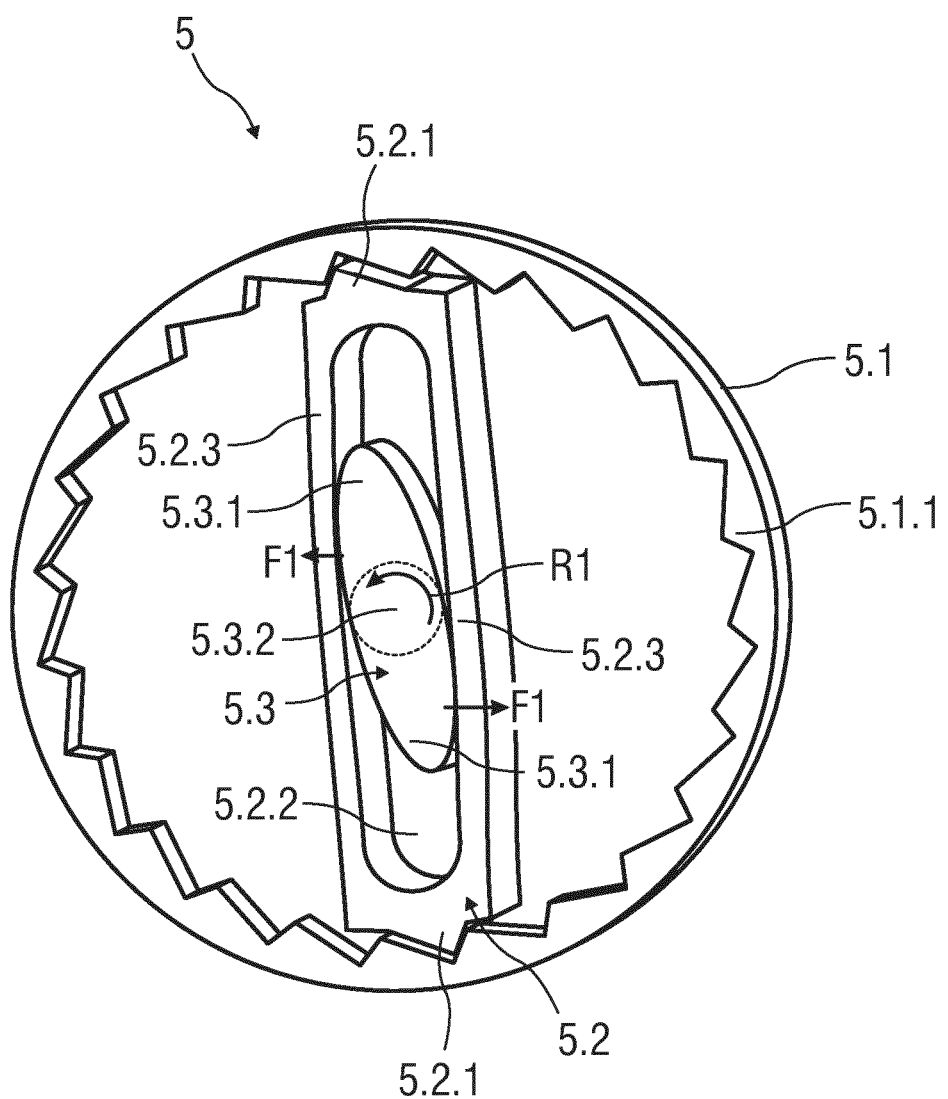
FIG. 4 is a schematic cross section of an exemplary embodiment of a released ratchet mechanism.

FIGS. 3 and 4 show a cross section of a first exemplary embodiment of a ratchet mechanism 5, wherein FIG. 3 illustrates the ratchet mechanism 5 in a locked state and FIG. 4 illustrates the ratchet mechanism 5 in a released state.

The ratchet mechanism 5 comprises a fixed ratchet element 5.1 having a circumferential teething 5.1.1. The circumferential teething 5.1.1 is formed by a number of teeth distributed about an inner circumference of the fixed ratchet element 5.1. The teeth respectively have a steep edge in one direction and a sloped edge in the opposite direction such that the ratchet flexible ratchet element is prevented from rotating in a rotation direction R1 (see FIG. 4, here counter clockwise) but is allowed to rotate in an opposite rotation direction (not illustrated). The fixed ratchet element 5.1 may be fixed to the housing 4 or coupled to the housing 4 in a manner being axially moveable with respect to the housing 4.

The ratchet mechanism 5 further comprises a flexible ratchet element 5.2 having a number of teethed portions 5.2.1 adapted to engage the circumferential teething 5.1.1. According to the present exemplary embodiment, the flexible ratchet element 5.2 is elongated shaped with a central elongated slot 5.2.2 limited by a perimeter 5.2.3 configured as two long sides, which are connected by the front ends. Thus, the flexible ratchet element 5.2 comprises two teethed portions 5.2.1 arranged on each front end of the flexible ratchet element 5.2 being arranged opposite each other. The teethed portions 5.2.1 respectively comprise one tooth with a steep edge and a slope edge corresponding with the configuration of the teeth of the circumferential teething 5.1.1. The flexible ratchet element 5.2 may be further formed of an elastic material, e. g. spring steel or fiber-reinforced plastic.

Moreover, the ratchet mechanism 5 comprises a rotational element 5.3 coupled to the dose setting handle 3 and arranged within the slot 5.2.2. The rotational element 5.3 comprises two cams 5.3.1 arranged about a shaft 5.3.2 that is immediately coupled to the dose setting handle 3. A length of the rotational element 5.3—according to an extension of the rotational coupling 5.3 between the cams 5.3.1—is greater than a width of the slot 5.2.2. Here, the width of the slot 5.2.2 means the extension of the slot 5.2.2 between the long sides of the flexible ratchet element 5.2.

Furthermore, the rotational element 5.3 and the dose setting handle 3 may be configured as one-piece being rotatable with respect to the flexible ratchet element 5.2. Upon application of torque onto the dose setting handle 3, the rotational element 5.3 rotates in a certain direction. The rotational element 5.3 is configured to translate the torque into a number of forces F1 radially acting onto the flexible ratchet element 5.2, in particular onto the perimeter 5.2.3 of the flexible ratchet element 5.2 arranged between the teethed portions 5.2.1 as illustrated in FIG. 4.

In FIG. 4, the ratchet mechanism 5 is locked in a given position representing a set dose, wherein the teethed portions 5.2.1 of the flexible ratchet element 5.2 are engaged pairwise to the circumferential teething 5.1.1. To set a dose of medicament, a user rotates the dose setting handle 3 in the opposite rotation direction until a desired dose is set. Subsequently, the engagement between the teethed portions 5.2.1 and the circumferential teething 5.1.1 is maintained by an engagement force F2, which counteracts the spring force of the strained drive spring 2. The engagement force F2 is provided by the stiffness of the material of the flexible ratchet element 5.2.

In order to dial down the set dose and thus overcoming the ratchet lock which prevents a rotation of the flexible ratchet element 5.2 in the rotation direction R1, the user applies torque onto the dose setting handle 3 in the rotation direction R1. As a result, the rotational element 5.3 and thus the cams 5.3.1 rotate into the rotation direction R1. Due to the proportion of dimensions of the slot 5.2.2 and the rotational element 5.3, the perimeter 5.2.3 of the flexible ratchet element 5.2 between the teethed portions 5.2.1—here the two long sides—is deflected in a radial outward direction. This deformation of the flexible ratchet element 5.2 leads to a reduction of a distance between the teethed portions 5.2.1 and thus to a disengagement of the teethed portions 5.2.1 and the circumferential teething 5.1.1. Finally, the ratchet lock is released and the flexible ratchet element 5.2 is allowed to rotate into the rotation direction R1 in order to incrementally dial down the pre-set dose.

Figure 5:
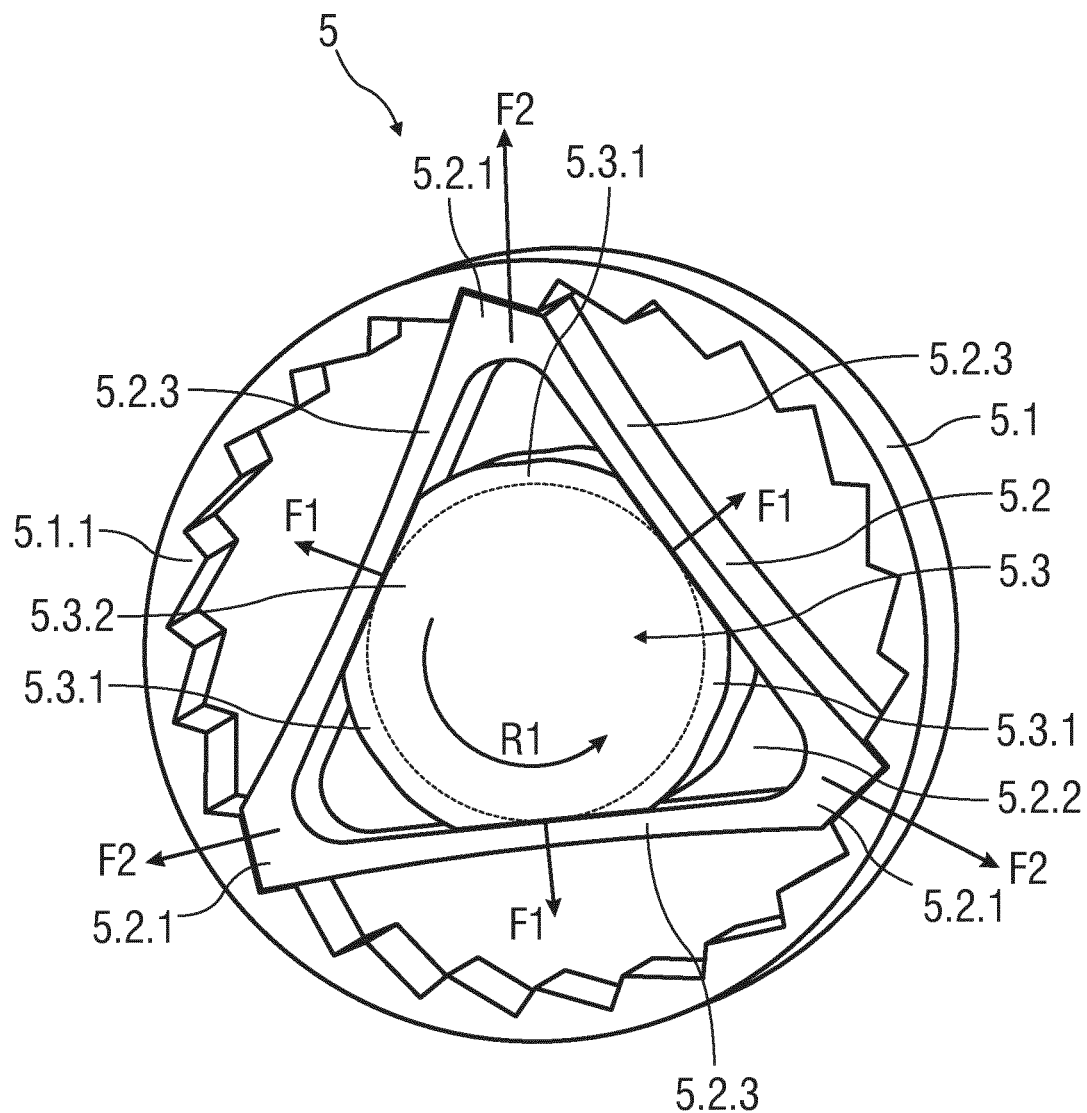
FIG. 5 is a schematic cross section of an alternative exemplary embodiment of a locked ratchet mechanism and FIG. 6 is a schematic cross section of a further alternative exemplary embodiment of a locked ratchet mechanism.

FIG. 5 shows a schematic cross section of a second exemplary embodiment of a locked ratchet mechanism 5.

The ratchet mechanism 5 comprises the fixed ratchet element 5.1 having a circumferential teething 5.1.1 similar to the fixed ratchet element 5.1 according to the first embodiment. In contrast to the first embodiment, the flexible ratchet element 5.2 of the second embodiment is triangular shaped, whereby the slot 5.2.2 comprises a corresponding triangular form limited by the perimeter 5.2.3, which comprises three sides connected by edges. Due to the triangular shape, the flexible ratchet element 5.2 is provided with three teethed portions 5.2.1 each arranged on one edge of the flexible ratchet element 5.2. The pairwise engagement of the teethed portions 5.2.1 and the circumferential teething 5.1.1 can be considered in a manner that two ends of each side of the triangular shaped flexible ratchet element 5.2 respectively represent one pair.

Similar to the first embodiment, the rotational element 5.3 is arranged within the slot 5.2.2 but comprises a shaft 5.3.2 with an increased diameter with respect to the shaft 5.3.2 of the first embodiment. Furthermore, the rotational element 5.3 comprises three cams 5.3.1 distributed about an outer circumference of the shaft 5.3.2. Due to the cams 5.3.1, the rotational element 5.3 comprises a non-circular shape similar to the rotational element 5.3 of the first embodiment.

According to the present embodiment, the ratchet mechanism 5 is in a locked stated, wherein the teethed portions 5.2.1 are in pairwise engagement with the circumferential teething 5.1.1 and wherein the cams 5.3.1 are in an angular position respectively facing one edge of the flexible ratchet element 5.2 and thus not abutting the perimeter 5.2.3 of the flexible ratchet element 5.2. Subsequently, the engagement between the teethed portions 5.2.1 and the circumferential teething 5.1.1 is maintained by the engagement force F2 similar to the first embodiment, whereby the engagement force F2 is increased with respect to the engagement force F2 provided in the first embodiment due to the increased number of teethed portions 5.2.1 that centers the engagement between the teethed portions 5.2.1 and the circumferential teething 5.1.1 within the fixed ratchet element 5.1. This also enables the use of stronger drive springs 2 with respect to the first embodiment.

In order to dial down the set dose and thus overcoming the ratchet lock which prevents a rotation of the flexible ratchet element 5.2 in the rotation direction R1, the user applies torque onto the dose setting handle 3 in the rotation direction R1. As a result, the rotational element 5.3 and thus the cams 5.3.1 rotate into the rotation direction R1. Due to the proportion of dimensions of the slot 5.2.2 and the rotational element 5.3, the perimeter 5.2.3 of the flexible ratchet element 5.2 between the teethed portions 5.2.1—here the three sides—is deflected in the radial outward direction. This deformation of the flexible ratchet element 5.2 leads to a reduction of a distance respectively between the pairs of teethed portions 5.2.1 and thus to a disengagement of the teethed portions 5.2.1 and the circumferential teething 5.1.1. Finally, the ratchet lock is released and the flexible ratchet element 5.2 is allowed to rotate into the rotation direction R1 in order to incrementally dial down the pre-set dose.

Figure 6:
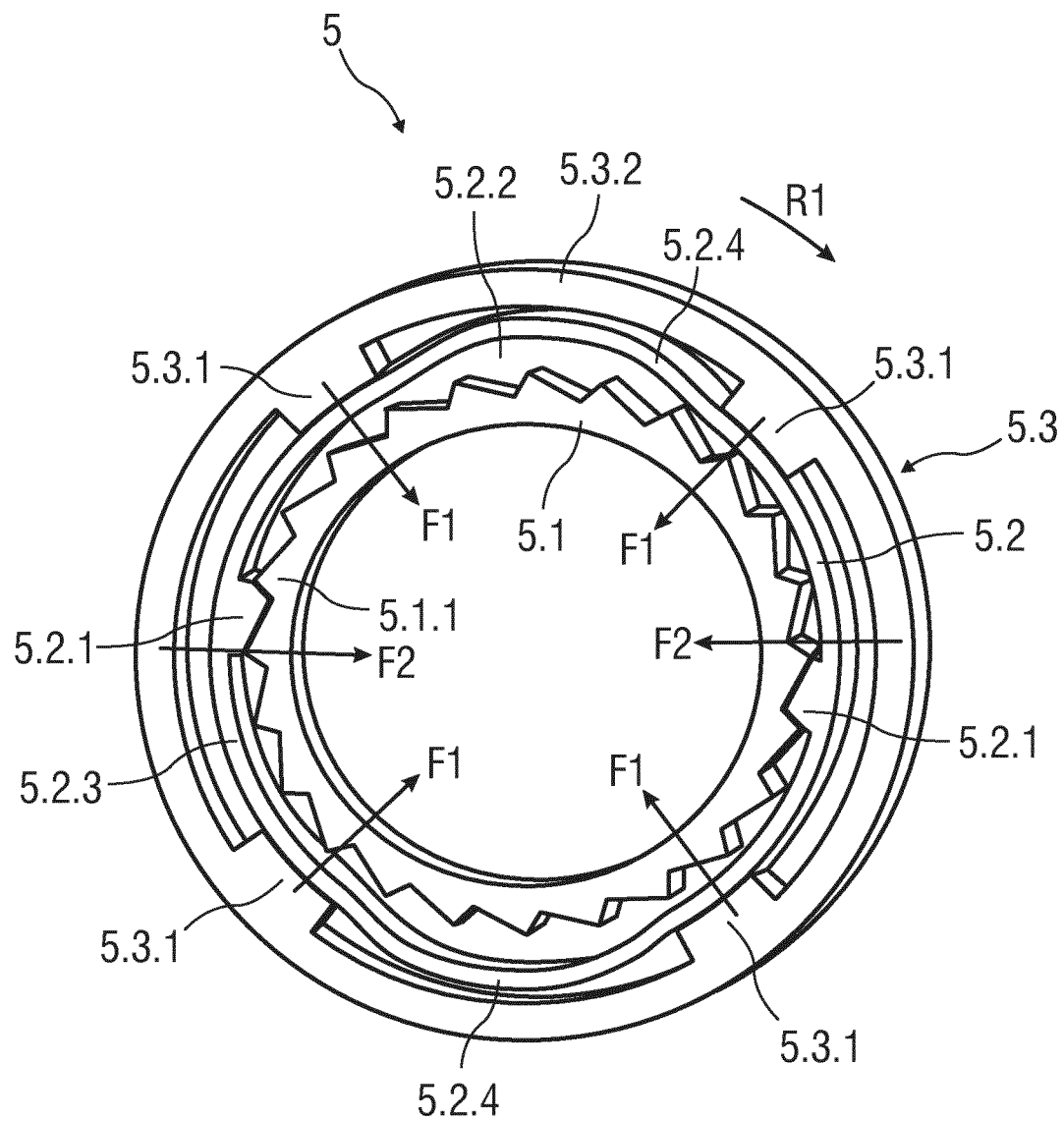

FIG. 6 shows a schematic cross section of a third exemplary embodiment of a locked ratchet mechanism 5.

In contrast to the first and the second embodiment, the circumferential teething 5.1.1 of the fixed ratchet element 5.1 is arranged about an outer circumference of the fixed ratchet element 5.1. The flexible ratchet element 5.2 is substantially ring-shaped and thus the slot 5.2.2 comprises a corresponding substantially circular form limited by the perimeter 5.2.3, which comprises a circumference of the substantially circular form. Due to the outer arrangement of the circumferential teething 5.1.1, the flexible ratchet element 5.2 is arranged out of the fixed ratchet element 5.1. Consequently, the fixed ratchet element 5.1 is arranged within the flexible ratchet element 5.2 in order to establish the engagement between the teethed portions 5.2.1 and the circumferential teething 5.1.1. According to the present embodiment, the flexible ratchet element 5.2 comprises two teethed portions 5.2.1 arranged opposite each other.

According further to the present embodiment, the rotational element 5.3 comprises a hollow shaft 5.3.2 that is ring-shaped as well as the fixed ratchet element 5.1 and the flexible ratchet element 5.2, whereby the rotational element 5.3 surrounds the flexible ratchet element 5.2. In particular, the fixed ratchet element 5.1, the flexible ratchet element 5.2 and the rotational element 5.3 are concentrically arranged within each other.

An inner diameter of the ring shaped shaft 5.3.2 is decreased by four cams 5.3.1 that are distributed about an inner circumference of the shaft 5.3.2 and that protrude in a radial inward direction facing the flexible ratchet element 5.2. Due to the decreased inner diameter, the flexible ratchet element 5.2 is deformed in a manner forming two bulges 5.2.4 respectively located between two cams 5.3.1 and between the teethed portions 5.2.1.

According to the present embodiment, the ratchet mechanism 5 is in a locked stated, wherein the teethed portions 5.2.1 are in pairwise engagement with the circumferential teething 5.1.1 and wherein respectively between two cams 5.3.1 one bulge 5.2.4 is located. In particular, the bulges 5.2.4 are located among cams 5.3.1 having no teethed portions 5.2.1 between. Subsequently, the engagement between the teethed portions 5.2.1 and the circumferential teething 5.1.1 is maintained by the engagement force F2 substantially similar to the first and second embodiment.

In order to dial down the set dose and thus overcoming the ratchet lock which prevents a rotation of the flexible ratchet element 5.2 in the rotation direction R1 (here clockwise), the user applies torque onto the dose setting handle 3 in the rotation direction R1. As a result, the rotational element 5.3 and thus the cams 5.3.1 rotate into the rotation direction R1. Due to the decreased inner diameter of the shaft 5.3.2 establishing the bulges 5.2.4 in the flexible ratchet element 5.2, the bulges 5.2.4 will be pushed in the rotation direction R1 until reaching the teethed portions 5.2.1, thereby disengaging the teethed portions 5.2.1 from the circumferential teething 5.1.1. Finally, the ratchet lock is released and the flexible ratchet element 5.2 is allowed to rotate into the rotation direction R1 in order to incrementally dial down the pre-set dose.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 1 injection device
2 drive spring
3 dose setting handle
4 housing
5 ratchet mechanism
5.1 fixed ratchet element
5.1.1 circumferential teething
5.2 flexible ratchet element
5.2.1 teethed portion
5.2.2 slot
5.2.3 perimeter
5.2.4 bulge
5.3 rotational element
5.3.1 cam
5.3.2 shaft
6 expelling mechanism
7 movable component
8 medicament container
9 needle
10 spindle-drive converter
10.1 spindle nut
11 plunger
12 stopper
13 dose setting mechanism
R1 rotation direction
F1 force
F2 engagement force

The invention claimed is:

1. A dose controlled multi-shot injection device comprising a housing and a dose setting mechanism, wherein the dose setting mechanism includes a drive spring,
a rotatable dose setting handle adapted to set a dose of medicament, thereby biasing the drive spring, and
a ratchet mechanism for maintaining the drive spring in a biased state against a spring force at the set dose,
wherein the ratchet mechanism includes
a fixed ratchet element coupled to the housing and having circumferential teething,
a movable flexible ratchet element provided with at least two teethed portions configured to engage the circumferential teething at least pairwise at any one of a plurality of engaging positions, which respectively represent the set dose, and
a rotational element coupled to the rotatable dose setting handle and configured to translate torque from the rotatable dose setting handle into a number of forces radially acting on the movable flexible ratchet element resulting in an elastic deformation of the movable flexible ratchet element, thereby releasing the engagement between the at least two teethed portions and the circumferential teething,
wherein upon application of the torque onto the rotatable dose setting handle, cams rotate with respect to the movable flexible ratchet element, wherein the cams are configured to deflect a perimeter of the movable flexible ratchet element in a radial outward direction in a manner reducing a distance between the at least two teethed portions.

2. The dose controlled multi-shot injection device according to claim 1, wherein the number of forces radially acting on the movable flexible ratchet element are applied to the perimeter of the movable flexible ratchet element arranged between the at least two teethed portions.

3. The dose controlled multi-shot injection device according to claim 1, wherein the number of forces acting on the movable flexible ratchet element has a same orientation as an engagement force provided by a structural stiffness of the movable flexible ratchet element.

4. The dose controlled multi-shot injection device according claim 1, wherein the rotational element comprises the cams, which rotate together with the rotatable dose setting handle and which rotate together with respect to the movable flexible ratchet element.

5. The dose controlled multi-shot injection device according to claim 1, wherein the fixed ratchet element comprises a ring-shape and the circumferential teething is arranged on an inner circumference of the fixed ratchet element.

6. The dose controlled multi-shot injection device according to claim 1, wherein the movable flexible ratchet element comprises an elongate shape with a central elongated slot and the at least two teethed portions are arranged opposite each other and the cams comprise two opposite cams on the rotational element within the central elongated slot.

7. The dose controlled multi-shot injection device according to claim 6, wherein the cams are coupled to the rotatable dose setting handle by a shaft arranged between the cams.

8. The dose controlled multi-shot injection device according claim 1, wherein the movable flexible ratchet element comprises a triangular shape with a central slot and the at least two teethed portions comprise three teethed portions each arranged on one edge of the movable flexible ratchet element and the cams comprise three cams provided on the rotational element within the central slot.

9. The dose controlled multi-shot injection device according to claim 1, further comprising a rotationally drivable expelling mechanism adapted to linearly urge against a movable component coupled to a medicament container.

10. The dose controlled multi-shot injection device according to claim 9, wherein the rotationally drivable expelling mechanism includes a spindle-drive converter.

11. The dose controlled multi-shot injection device according to claim 9, wherein the medicament container contains the medicament.

12. A dose controlled multi-shot injection device comprising a housing and a dose setting mechanism, wherein the dose setting mechanism includes
   a drive spring,
   a rotatable dose setting handle adapted to set a dose of medicament, thereby biasing the drive spring, and
   a ratchet mechanism for maintaining the drive spring in a biased state against a spring force at the set dose,
   wherein the ratchet mechanism includes
   a fixed ratchet element coupled to the housing and having a circumferential teething,
   a movable flexible ratchet element provided with at least two teethed portions configured to engage the circumferential teething at least pairwise at any one of a plurality of engaging positions, which respectively represent the set dose, and
   a rotational element coupled to the rotatable dose setting handle and configured to translate torque from the rotatable dose setting handle into a number of forces radially acting on the movable flexible ratchet element resulting in an elastic deformation of the movable flexible ratchet element, thereby releasing the engagement between the at least two teethed portion and the circumferential teething,
   wherein the fixed ratchet element comprises a ring-shape and the circumferential teething is arranged on an outer circumference of the fixed ratchet element,
   wherein the movable flexible ratchet element is ring-shaped and comprises the at least two teethed portions arranged opposite each other on an inner circumference, the rotational element comprises a ring-shaped shaft and at least four cams, which are distributed about an inner circumference of the ring-shaped shaft, decreasing an inner diameter of the ring-shaped shaft and facing the movable flexible ratchet element, and
   wherein the movable flexible ratchet element is arranged between the rotational element and the fixed ratchet element such that the at least four cams abut a perimeter of the movable flexible ratchet element and the at least two teethed portions face the circumferential teething.

13. The dose controlled multi-shot injection device according to claim 2, wherein the movable flexible ratchet element comprises at least two bulges respectively located between the at least two teethed portions due to the decreased inner diameter of the ring-shaped shaft.

14. The dose controlled multi-shot injection device according to claim 13, wherein upon application of torque onto the rotatable dose setting handle, the at least four cams rotate with respect to the movable flexible ratchet element, wherein the at least four cams are configured to push the at least two bulges in a same rotation direction as the rotational element, and wherein the at least two teethed portions are disengaged from the circumferential teething when the at least two bulges reach the at least two teethed portions respectively.

15. The dose controlled multi-shot injection device according to claim 12, further comprising a rotationally drivable expelling mechanism adapted to linearly urge against a movable component coupled to a medicament container.

16. The dose controlled multi-shot injection device according to claim 15, wherein the rotationally drivable expelling mechanism includes a spindle-drive converter.

* * * * *

UNITED STATES PATENT AND TRADEMARK OFFICE
CERTIFICATE OF CORRECTION

PATENT NO. : 11,135,376 B2
APPLICATION NO. : 16/084870
DATED : October 5, 2021
INVENTOR(S) : Markus Ploch It is certified that error appears in the above-identified patent and that said Letters Patent is hereby corrected as shown below:

In the Claims

Column 12, Line 40, Claim 4, before "claim", insert -- to --

Column 12, Line 58, Claim 8, before "claim", insert -- to --

Column 14, Line 13, Claim 13, delete "claim 2," and insert -- claim 12, --

Signed and Sealed this
Third Day of May, 2022

Katherine Kelly Vidal
*Director of the United States Patent and Trademark Office*